US012290783B2

(12) United States Patent
Joshi et al.

(10) Patent No.: US 12,290,783 B2
(45) Date of Patent: May 6, 2025

(54) CONVERTING GASEOUS CARBON COMPOUNDS TO CARBON NEUTRAL OR NEGATIVE PRODUCTS

(71) Applicant: Woodside Energy Technologies Pty Ltd, Perth (AU)

(72) Inventors: Jitendra Achyut Joshi, Perth (AU); Min Ao, Redcliffe (AU); Michael Edward Lev Massen-Hane, Cambridge, MA (US); Qiqing Shen, Bentley (AU); Sui Boon Liaw, Maddington (AU); Alexander David Simons, Cottesloe (AU)

(73) Assignee: Woodside Energy Technologies Pty Ltd, Perth (AU)

( * ) Notice: Subject to any disclaimer, the term of this patent is extended or adjusted under 35 U.S.C. 154(b) by 0 days.

(21) Appl. No.: 18/348,680

(22) Filed: Jul. 7, 2023

(65) Prior Publication Data
US 2023/0347287 A1    Nov. 2, 2023

Related U.S. Application Data

(63) Continuation of application No. PCT/AU2022/050883, filed on Aug. 11, 2022.

(30) Foreign Application Priority Data

Aug. 12, 2021 (AU) .................. 2021902515

(51) Int. Cl.
*B01D 53/84* (2006.01)
*B01D 53/34* (2006.01)
(Continued)

(52) U.S. Cl.
CPC .......... *B01D 53/84* (2013.01); *B01D 53/346* (2013.01); *C12M 47/18* (2013.01); *C12N 1/20* (2013.01);
(Continued)

(58) Field of Classification Search
None
See application file for complete search history.

(56) References Cited

U.S. PATENT DOCUMENTS

| | | | | |
|---|---|---|---|---|
| 4,044,500 A | * | 8/1977 | Hitzman | A01G 33/00 435/813 |
| 6,180,396 B1 | * | 1/2001 | Ono | C12M 47/18 422/150 |

(Continued)

FOREIGN PATENT DOCUMENTS

| | | |
|---|---|---|
| EP | 3730457 A1 | 10/2020 |
| JP | 2020 005599 A | 1/2020 |

(Continued)

OTHER PUBLICATIONS

Acosta et al. "Microbial protein production from methane via electrochemical biogas upgrading." Chemical Engineering Journal 391 (2020) 123625. (Year: 2020).*

(Continued)

*Primary Examiner* — William H. Beisner
(74) *Attorney, Agent, or Firm* — Edell, Shapiro & Finnan, LLC (57) ABSTRACT

Gaseous carbon compounds can be converted to carbon neutral or negative products using biological processes to metabolise the gaseous carbon compounds or use thermochemical processes to convert gaseous carbon compounds to syngas followed by thermochemical or biological processes to produce products. The gaseous carbon compounds include a mixture of $CO_2$ and $CH_4$ from either a single source, or two or more different sources. Separate biological processes are incorporated to process different gaseous carbon compounds. A gaseous carbon compound produced as a by-product of one biological process can be used as at least part of the feedstock for another process. A renewable energy system can be provided to power equipment. A (Continued)

control system can be used to control flow of gaseous carbon compounds and reactants entering the entire carbon processing systems to provide mass balanced quantities of gaseous carbon compounds and reactants in each processing system and/or between processing systems.

19 Claims, 4 Drawing Sheets

(51) Int. Cl.
*C12M 1/00* (2006.01)
*C12N 1/20* (2006.01)
(52) U.S. Cl.
CPC .. *B01D 2251/102* (2013.01); *B01D 2251/202* (2013.01); *B01D 2251/95* (2013.01); *B01D 2257/504* (2013.01); *B01D 2257/7025* (2013.01)

(56) References Cited

U.S. PATENT DOCUMENTS

| | | | |
|---|---|---|---|
| 2007/0029264 A1* | 2/2007 | Bowe | C12M 43/08 210/603 |
| 2010/0000874 A1 | 1/2010 | Hinman et al. | |
| 2010/0022669 A1 | 1/2010 | Cohn et al. | |
| 2012/0226080 A1 | 9/2012 | Meyer-Pittroff | |
| 2013/0040349 A1 | 2/2013 | Heichberger | |
| 2013/0149755 A1* | 6/2013 | Reed | C12P 7/6463 204/278 |
| 2014/0194539 A1 | 7/2014 | Hammad et al. | |
| 2019/0390158 A1 | 12/2019 | Dyson et al. | |
| 2020/0010861 A1* | 1/2020 | Yu | C12M 29/18 |
| 2020/0181659 A1* | 6/2020 | Hickey | C12P 7/625 |
| 2020/0283362 A1 | 9/2020 | MacGregor | |
| 2020/0347417 A1 | 11/2020 | Herrema | |
| 2021/0024861 A1 | 1/2021 | He et al. | |
| 2021/0164001 A1* | 6/2021 | Al Rowaihi | C12M 21/12 |
| 2021/0221753 A1 | 7/2021 | Gillespie | |

FOREIGN PATENT DOCUMENTS

| | | | | |
|---|---|---|---|---|
| WO | WO-2009010347 A2 * | 1/2009 | | C01B 3/382 |
| WO | 2012110257 A1 | 8/2012 | | |
| WO | 2021203176 A1 | 10/2021 | | |

OTHER PUBLICATIONS

International Search Report and Written Opinion in International Application No. PCT/AU2022/050883, dated Nov. 4, 2022, 14 pages.
Reza Salehi et al., Conversion of biogas from anaerobic digestion to single cell protein and bio-methanol: mechanism, microorganisms and key factors—a review, Environ. Eng. Res. 2022; 27(4):210109, Jun. 21, 2021, 14 pages.
Verbreeck, Kristof et al., Assessing the potential for up-recycling recovered resources from anaerobic digestion through microbial protein production, Microbial Biotechnology, 14(3), May 1, 2021, 14 pages.
Australian Patent Office International-Type Search Report for AU 2021902515, mailed Jun. 30, 2022, 25 pages.
Written Opinion of the International Preliminary Examining Authority in International Application No. PCT/AU2022/050883, dated May 10, 2023, 9 pages.
Strobel, G. et al., Underground bio-methanation: Concept and potential, Renewable and Sustainable Energy Reviews, 123:109747, Feb. 20, 2020, 11 pages.
Extended European Search Report in counterpart European Application No. 22854804.6, mailed Jun. 10, 2024, 11 pages.
Verbeeck Kristof et al: "Assessing the potential for up-cycling recovered resources from anaerobic digestion through microbial protein production", Microbial Biotechnology, vol. 14, No. 3, Jun. 11, 2020 (Jun. 11, 2020), pp. 897-910, XP093035699, GB ISSN: 1751-7915, DOI: 10.1111/1751-7915.13600.
Salehi Reza et al: "Conversion of biogas from anaerobic digestion to single cell protein and bio-methanol: mechanism, microorganisms and key factors—a review", Environmental Engineering Research, vol. 27, No. 4, Jun. 21, 2021 (Jun. 21, 2021), pp. 210109-1, XP093035694, ISSN: 1226-1025, DOI: 10.4491/eer.2021.109, pp. 2-5; figure 1.
Linder Tomas Ed—Grafton Quentin et al: "Making the case for edible microorganisms as an integral part of a more sustainable and resilient food production system", Food Security, Springer Netherlands, Dordrecht, vol. 11, No. 2, Mar. 22, 2019 (Mar. 22, 2019), pp. 265-278, XP036811013, ISSN: 1876-4517, DOI: 10.1007/SI2571-019-00912-3 [retrieved on Mar. 22, 2019], pp. 270,271; figure 2.
Khoshnevisan Benyamin et al: "From renewable energy to sustainable protein sources: Advancement, challenges, and future roadmaps", Renewable and Sustainable Energy Reviews, Elseviers Science, New York, NY, US, vol. 157, Jan. 1, 2022 (Jan. 1, 2022), XP086955830, ISSN: 1364-0321, DOI: 10.1016/J.RSER.2021.112041 [retrieved on Jan. 1, 2022], pp. 3-5, 13, p. 15; figures 1, 2.

* cited by examiner

CONVERTING GASEOUS CARBON COMPOUNDS TO CARBON NEUTRAL OR NEGATIVE PRODUCTS

CROSS-REFERENCE TO RELATED APPLICATIONS

This application is a continuation of International Application No. PCT/AU2022/050883, filed Aug. 11, 2022, which claims priority to Australian Application No. AU 2021902515, filed Aug. 12, 2021, the disclosures of which are incorporated herein by reference in their entireties.

TECHNICAL FIELD

A system and method for converting gaseous carbon compounds to carbon neutral or negative products is disclosed. The gaseous carbon may derive from one, or a combination of, sources including but not limited to: fossil fuels; extracted from the atmosphere; or organic waste processes, such as landfill biogas or animal waste. The carbon neutral or negative products may include, but are not limited to: feed protein for animals, pharmaceuticals, and high-value chemicals.

BACKGROUND

The growing concerns over global warming have provoked substantial research in greenhouse gases. It has been widely agreed that to limit the temperature increase below 1.5° C., multiple methods need to be implemented to not only reduce the emission of greenhouse gases, particularly carbon dioxide and methane, but also decrease the current contents of greenhouse gases in atmosphere. While carbon dioxide is well-known for its greenhouse effect, methane has about 28 times higher Global Warming Potential (GWP) than carbon dioxide over 100 years. As a result, diminishing methane emission from its various sources must not be overlooked. In 2021, US, EU, and other 103 countries lunched a Global Methane Pledge, intended to reduce global methane emissions by at least 30 percent from 2020 levels by 2030.

Research has been focusing on various ways to utilise the greenhouse gases to valuable products. For example, the Switzerland company Climeworks has several operational plants to directly capture carbon dioxide from the atmosphere, with a collective capacity of 2,000 tonnes per year. The captured carbon dioxide will be permanently stored via natural underground mineralization. Some companies, e.g., Carbon Engineering, are developing technologies to convert carbon dioxide to synthetic fuels through multiple reactions. Methane itself is a valuable energy source but 55-70% of methane emission is caused by biogenic sources, such as livestock farming, landfill, and wetlands, which cannot be captured as used as nature gas. In some thermochemical technologies, methane is converted with carbon dioxide as the reduction chemical to produce syngas, which is an important precursor of various chemicals and fuels. Research has shown that algae, bacteria, and other microorganisms have huge potential to consume gaseous carbon through photosynthetic or metabolic processes. Hitherto the economics of greenhouse gas extraction has been a stumbling block to large-scale commercially viable operations.

It is believed that an approach to the extraction and conversion of carbon from gaseous compounds to commercial products as disclosed herein may help in keeping global warming to or preferably below the 1.5° C. target.

The above references to the background art do not constitute an admission that the art forms a part of the common general knowledge of a person of ordinary skill in the art. The above references are also not intended to limit the application of the disclosed system and method to any particular form of the system and method.

SUMMARY OF THE DISCLOSURE

In one aspect there is disclosed an integrated system for converting gaseous carbon compounds to carbon neutral or negative products comprising:
  a source capable of producing a mixed of gaseous carbon feedstock which includes carbon dioxide and methane;
  a biological methane processing system containing methane metabolising microorganisms and fed with methane from the source, the biological methane processing system arranged to: propagate methane metabolising microorganisms; and, produce carbon dioxide as a by-product;
  a biological carbon dioxide processing system containing carbon dioxide metabolising microorganisms and fed with carbon dioxide from the source of mixed of gaseous carbon feedstock and the carbon dioxide by-product, the biological carbon dioxide processing system arranged to: propagate carbon dioxide metabolising microorganisms; and
  a microorganism harvesting and processing system arranged to harvest the propagated microorganisms and produce a single cell protein.

In one embodiment the methane metabolising microorganisms comprise mesophilic methanotrophic bacterium.

In one embodiment the carbon dioxide metabolising microorganisms comprise mesophilic bacterium.

In one embodiment the carbon dioxide metabolising microorganisms comprise cyanobacteria.

In one embodiment the carbon dioxide metabolising microorganisms comprise hydrogenotrophic bacteria.

In one embodiment the integrated system comprises an air separation unit capable of producing gaseous oxygen and wherein the integrated system is arranged to feed the gaseous oxygen to one or both of the biological methane processing system, and the biological carbon dioxide processing system.

In one embodiment the integrated system comprises a water splitting unit capable of producing gaseous oxygen and wherein the integrated system is arranged to feed the gaseous oxygen to one or both of the biological methane processing system, and the biological carbon dioxide processing system.

In one embodiment the integrated system comprises a water separation unit capable of producing gaseous hydrogen and wherein the integrated system is arranged to feed the gaseous hydrogen to one or both of the biological methane processing system, and the biological carbon dioxide processing system.

In one embodiment the integrated system comprises a cooling system operable to cool one or both of the biological methane processing system, and the biological carbon dioxide processing system to operate within a predetermined temperature range.

In one embodiment the microorganism harvesting and processing system includes: a first harvesting system for harvesting microorganisms from the biological methane processing system; a second harvesting system for harvesting microorganisms from the biological carbon dioxide processing system; and a common a dryer for drying the harvested microorganisms harvested by both the first and second harvesting systems.

In one embodiment the integrated system comprises a renewable energy system capable of converting energy from one or more renewable energy sources into one or more forms of controlled energy; and wherein one or both of the biological methane processing system, and the biological carbon dioxide processing system are powered by the controlled energy.

In one embodiment one or more of the water splitting unit; the air separation unit; the cooling system; and the microorganism harvesting and processing system are powered by the controlled energy.

In a second aspect there is disclosed an integrated biological method for converting gaseous carbon compounds to carbon neutral or negative products comprising:
feeding gaseous methane from a first biogas source to a biological methane processing system capable of propagating methanotrophic bacterium and producing carbon dioxide as a by-product;
feeding (a) gaseous carbon dioxide from the first biogas source, and (b) the carbon dioxide by-product, to a biological carbon dioxide processing system capable of propagating a carbon dioxide metabolising bacterium; and
producing a single cell protein from the propagated methanotrophic bacterium and the propagated carbon dioxide metabolising bacterium.

In one embodiment feeding the gaseous methane and feeding the gaseous carbon dioxide from the first biogas source includes feeding biogas comprising a mixture of gaseous methane and gaseous carbon dioxide from the first biogas source to a gas pre-treatment and separation unit and operating the gas pre-treatment and separation unit to provide separate gaseous methane and gaseous carbon dioxide feed streams.

In one embodiment the method comprises supplying gaseous oxygen to the biological methane processing system.

In one embodiment the method comprises supplying gaseous oxygen to the biological carbon dioxide processing system.

In one embodiment the method comprises supplying gaseous hydrogen to the biological carbon dioxide processing system.

In one embodiment the method comprises using hydrogenotrophic bacteria as the carbon dioxide metabolising bacterium.

In one embodiment the method comprises using cyanobacteria as the carbon dioxide metabolising bacterium.

In one embodiment the method comprises supplying one or more nutrients to one or both of the biological methane processing system and the biological carbon dioxide processing system.

In one embodiment the method comprises cooling one or both of the biological methane processing system, and the biological carbon dioxide processing system to operate within a predetermined temperature range.

In one embodiment supplying the gaseous oxygen comprises producing gaseous oxygen from one or both of (a) an air separation unit, and (b) a water splitting unit.

In one embodiment supplying the gaseous hydrogen comprises operating a water splitting unit to produce the supplied gaseous hydrogen.

In one embodiment producing the single cell protein comprises harvesting and drying the propagated methanotrophic bacterium and the propagated carbon dioxide metabolising bacterium In one embodiment the method comprises generating power from one or more renewable energy sources and using the generated power to as operating power for plant and equipment used to enable performance of the method.

In a third aspect there is disclosed a method of animal husbandry comprising:
producing biogas from waste products excreted by a plurality of animal wherein the biogas includes a mixture of gaseous methane and carbon dioxide;
converting the biogas to single cell proteins using the method according to the second aspect; and feeding the plurality of animals with food comprising the single cell proteins.

In a fourth aspect there is disclosed a carbon processing system for generating one or more carbon neutral products comprising:
a renewable energy system capable of converting energy from one or more renewable energy sources into one or more forms of controlled energy;
one or more sources of gaseous carbon compounds;
a feed stream of one or more reactants; and
a carbon processing plant powered by the controlled energy and
arranged to convert the gaseous carbon compounds in the presence of the one or more reactants to produce one or more vendible products.

In one embodiment of the fourth aspect the one or more sources of gaseous carbon compounds comprise a direct air carbon capture system powered by the renewable energy system.

In one embodiment of the fourth aspect the one or more sources of gaseous carbon compounds comprises a methane source.

In one embodiment of the fourth aspect the methane source comprises an oil or gas reservoir.

In one embodiment of the fourth aspect the methane source comprises coal seam gas.

In one embodiment of the fourth aspect the methane source comprises bio-waste.

In one embodiment of the fourth aspect the reactants comprise one or more of oxygen, hydrogen and water.

In one embodiment of the fourth aspect the carbon processing system comprises an air separation unit for producing oxygen wherein the air separation unit is driven by the renewable energy system.

In one embodiment of the fourth aspect the carbon processing system comprises a water splitting unit for producing the oxygen or hydrogen wherein the water splitting unit is driven by the renewable energy system.

In one embodiment of the fourth aspect the carbon processing system comprises a methane pyrolysis unit for producing the hydrogen wherein the methane pyrolysis unit is driven by the renewable energy conversion system.

In one embodiment of the fourth aspect the carbon processing plant comprises one or more carbon processing units arranged to process the gaseous carbon compound in the presence of one or more of the reactants to produce the one or more vendible products.

In one embodiment of the fourth aspect the one or more carbon processing units comprise bio-reactors for biologically processing the gaseous carbon compound.

In one embodiment of the fourth aspect the one or more carbon processing units comprise a dissociation unit arrange to dissociate carbon from other elements in the gaseous carbon compound.

In one embodiment of the fourth aspect at least one of the carbon processing units is arranged to produce gaseous carbon dioxide, and the carbon capture and processing system is arranged to feed the produced carbon dioxide to at least one other of the carbon processing units.

In one embodiment of the fourth aspect the renewable energy system comprises a concentrated solar thermal plant which heats a flowable heat transfer and storage medium.

In one embodiment of the fourth aspect the renewable energy system comprises a photovoltaic array for producing electricity to drive the carbon capture and processing system.

In one embodiment of the fourth aspect the renewable energy system is arranged to store energy to enable diurnal operation of the carbon capture and processing system.

In a fifth aspect there is disclosed a method processing carbon for generating one or more carbon neutral products comprising:
producing energy using a renewable energy;
feeding one or more gaseous carbon compounds to a carbon processing plant;
feeding one or more reactant to the carbon processing plant;
using the produced energy to drive at least the carbon processing plant; and
operating the carbon processing plant to convert the gaseous carbon compounds in the presence of the one or more reactants into one or more vendible carbon neutral products.

In one embodiment of the fifth aspect feeding the one or more gaseous carbon compounds comprises feeding gaseous carbon dioxide derived from any one or more of: (a) a direct air carbon capture system which is driven by the produced energy; (b) production, processing or combustion of a fossil fuel; and (c) a by-product or waste product of an industrial process including cement manufacture or ammonia production.

In one embodiment of the fifth aspect feeding gaseous carbon compounds comprises feeding methane to the carbon processing plant.

In one embodiment of the fifth aspect feeding methane comprises feeding methane sourced from an oil or gas reservoir.

In one embodiment of the fifth aspect feeding methane comprises feeding methane sourced from a coal seam.

In one embodiment of the fifth aspect feeding methane comprises feeding methane sourced from bio-waste.

In one embodiment of the fifth aspect feeding the one or more reactant comprises feeding one or more of oxygen, hydrogen, and water feed streams.

In one embodiment of the fifth aspect feeding oxygen comprises feeding oxygen produced by an air separation unit driven by the produced energy.

In one embodiment of the fifth aspect feeding oxygen comprises feeding oxygen produced by a water splitting unit driven by the produced energy.

In one embodiment of the fifth aspect feeding hydrogen comprises feeding hydrogen produced by a water splitting unit or a methane pyrolysis unit driven by the produced energy.

In one embodiment of the fifth aspect the method comprises forming the carbon processing plant as one or more carbon processing units each capable of processing the gaseous carbon compounds in the presence of one or more of the reactants to produce the one or more vendible products or a precursor for a vendible product.

In one embodiment of the fifth aspect at least one of carbon processing units is arranged to biologically process the gaseous carbon compound.

In one embodiment of the fifth aspect at least one of the carbon processing units is a dissociation unit arranged to dissociate carbon from other elements in the gaseous carbon compound.

In one embodiment of the fifth aspect feeding gaseous carbon dioxide produced as a waste product by a process within the carbon processing plant back to the carbon processing plant.

In one embodiment of the fifth aspect the method comprises operating the renewable energy system as a concentrated solar thermal plant wherein the produced energy is thermal energy carried in and by a flowable heat transfer medium.

In one embodiment of the fifth aspect the method comprises operating the renewable energy system in a manner wherein the produced energy includes electrical energy.

In one embodiment of the fifth aspect the method comprises storing at least a proportion of the produced energy and subsequently using the stored energy to enable diurnal operation of the carbon capture and processing system.

In one embodiment of the fifth aspect the method comprises monitoring and controlling flow of the gaseous carbon compound and the reactants to the carbon processing units to provide mass balanced quantities of the gaseous carbon compound and the reactants for the process performed in each carbon processing unit.

In a sixth aspect there is disclosed integrated system for converting gaseous carbon compounds to carbon neutral or negative products comprising:
a renewable energy system capable of converting energy from one or more renewable energy sources into one or more forms of controlled energy;
one or more sources of one or more gaseous carbon compounds;
a feed stream of one or more reactants; and
a carbon processing plant powered by the controlled energy and arranged to convert the gaseous carbon compounds in the presence of the one or more reactants to produce one or more vendible products, the carbon processing plant having: a first carbon processing unit capable of producing, from at least one of the gaseous carbon compounds, a first vendible product and a gaseous carbon compound by-product; and, a second carbon unit capable of producing from the gaseous carbon compound by-product a second vendible product.

In one embodiment one or both of the first and second carbon processing unit comprise bioreactors that biologically process the gaseous carbon compounds.

In one embodiment the first carbon processing unit is a biological methane processing system containing methane metabolising microorganisms, and the gaseous carbon compound by-product is carbon dioxide.

In one embodiment the methane metabolising microorganisms comprise mesophilic methanotrophic bacterium.

In one embodiment the second carbon processing unit is a biological carbon dioxide processing system containing carbon dioxide metabolising microorganisms.

In one embodiment the carbon dioxide metabolising microorganisms comprise mesophilic bacterium.

In one embodiment the carbon dioxide metabolising microorganisms comprise cyanobacteria.

In one embodiment the carbon dioxide metabolising microorganisms comprise hydrogenotrophic bacteria.

In one embodiment the integrated system comprises a third carbon processing unit capable of producing a third vendible product, the third carbon processing unit being a biological carbon dioxide processing system containing carbon dioxide metabolising microorganisms, wherein the carbon dioxide metabolising microorganisms of the second carbon processing unit comprise hydrogenotrophic bacteria and the carbon dioxide metabolising microorganisms of the third carbon processing unit comprise cyanobacteria.

In one embodiment the carbon processing plant includes a syngas generation unit capable of producing syngas from the from the one or more gaseous carbon compounds and the gaseous carbon compound by-product.

In a seventh aspect there is disclosed a system for converting gaseous carbon compounds to carbon neutral or negative products comprising:
   a renewable energy system capable of converting energy from one or more renewable energy sources into one or more forms of controlled energy;
   one or more sources of methane and carbon dioxide;
   a syngas generation unit capable of forming a syngas from the methane and carbon dioxide, the syngas generation unit being powered by the controlled energy; and
   a syngas conversion unit arranged to convert the syngas into a carbon neutral or carbon negative product.

In one embodiment the syngas conversion unit is a bioreactor capable of fermenting the syngas.

In one embodiment the syngas conversion unit is arranged to perform a thermochemical process to produce a hydrocarbon.

BRIEF DESCRIPTION OF THE DRAWINGS

Notwithstanding any other forms which may fall within the scope of the system and method as set forth in the Summary, specific embodiments will now be described, by way of example only, with reference to becoming drawings in which.

DETAILED DESCRIPTION OF SPECIFIC EMBODIMENTS

Specific embodiments of the disclosed system and method will now be described by way of example only. The terminology used herein is for the purpose of describing particular embodiments only, and is not intended to limit the scope of the disclosed system and method. Unless defined otherwise, all technical and scientific terms used herein have the same meanings as commonly understood by one of ordinary skill in the art to pertaining to system and method. In the drawings, it should be understood that like reference numbers refer to like parts.

The general idea disclosed herein is to provide a system and method for converting gaseous carbon compounds to carbon neutral or negative products. The gaseous carbon compounds may be provided from one or more sources. A source may provide: a single gaseous carbon compound, for example CO2 or CH4; or mixed gaseous carbon compounds, for example both CO2 and CH4. Separate biological processes are incorporated to process different gaseous carbon compounds. A gaseous carbon compound produced as a waste product of one biological process may be used as the, or part of the, feedstock for another biological process.

The system and method also contemplate the provision of feed streams of other reactants such as oxygen, hydrogen and water to facilitate the processing of the gaseous carbon compounds. The processes which consume the gaseous carbon compounds include but are not limited to bioreactions such as metabolisation/fermentation and/or, chemical disassociation. In some embodiments only biological processes are used to consume gaseous carbon compounds. To assist in minimising carbon footprint and enabling an overall carbon negative profile, a renewable energy system may be provided to power the individual processes, systems and apparatus in various embodiment of the disclosed integrated system and method.

Figure 1:
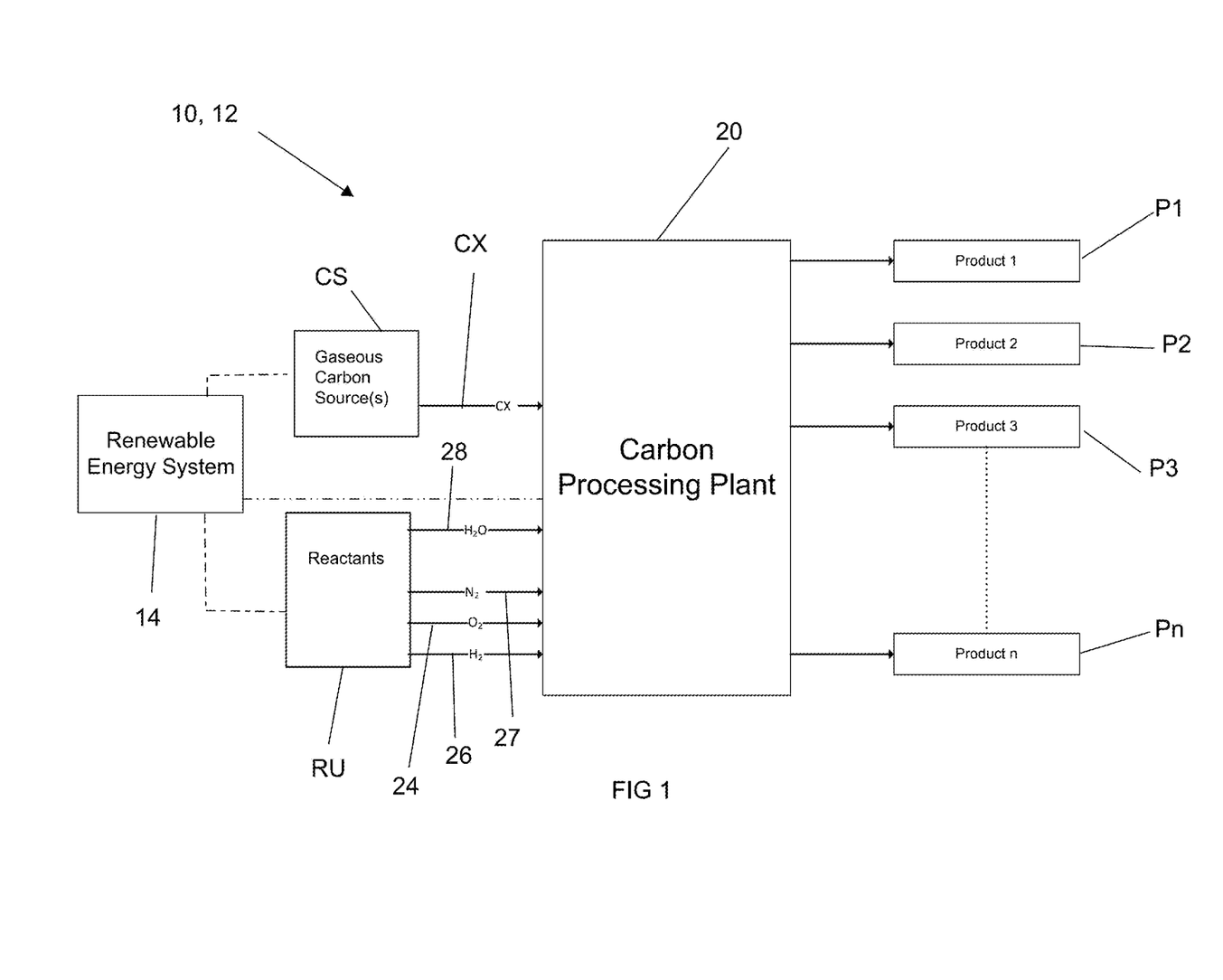
FIG. 1 is a flow diagram broadly illustrating one embodiment of the disclosed system and method for converting gaseous carbon compounds to carbon neutral or negative products.

FIG. 1 broadly illustrates, in the form of a flow diagram, an embodiment of the disclosed system 10 and associated method 12 for capturing gaseous carbon compounds and processing that carbon to produce valuable products.

In the system 10 and method 12 energy from one or more renewable energy sources is converted by a renewable energy system 14 into one or more forms of energy that are controlled and used to drive downstream plant, equipment and processes. For example, the renewable energy system 14 may be arranged to produce both heat energy and electricity. The energy conversion system 14 may also include energy storage facilities such as a volume of a molten salt or particulate material for storing heat, and/or a battery for storing electricity. Depending on the application, the energy storage facilities will be adapted to enable 24/7 operation of the system 10.

One or more gaseous carbon compounds CX are provided by one or more gaseous carbon source(s) CS to a carbon processing plant 20. The gaseous carbon compounds may be different compounds/gases, for example carbon dioxide and methane. The gaseous carbon source(s) CS may comprise a single source, or a combination of sources. Any gaseous carbon source may also provide a mixture of two or more different gaseous carbon compounds. For example, gaseous carbon source(s) CS may comprise a biogas source that provides a mixture of methane and carbon dioxide, (as well as other non-carbon gases such as nitrogen, hydrogen sulphide and ammonia).

Energy from the system 14 may be used to power one or more of the gaseous carbon source(s) CS that convert or process a material to produce a stream of gaseous carbon compound(s) CX. The stream CX is fed to a carbon processing plant 20. The carbon processing plant may have a number of different processing systems to produce a range of different products P1-Pn. Different processes within the carbon processing unit are arranged to process different forms of gaseous carbon compounds or perform different processes on the gaseous carbon compounds to produce different products P1-Pn. Energy to operate the carbon processing plant 20 is provided by the renewable energy system 14.

Other reactants and/or nutrients may be provided to the carbon processing plant 20 to facilitate or augment particular processes for producing specific products P1-Pn. Examples of the reactants include one or more of: oxygen, hydrogen, nitrogen and water provided by respective feed streams 24, 26, 27 and 28. The nutrients, if and when provided may comprise macronutrients and/or micro nutrients. As discussed later one or more of the reactants may be produced by respective reactant generation units RU. The units RU may be powered by the renewable energy system 14.

The products P1-Pn may include single cell protein that can be used as animal feed, artificial meat for human consumption, pharmaceuticals, high-value chemicals such as ethanol, isopropanol, and palm oil.

Figure 2:
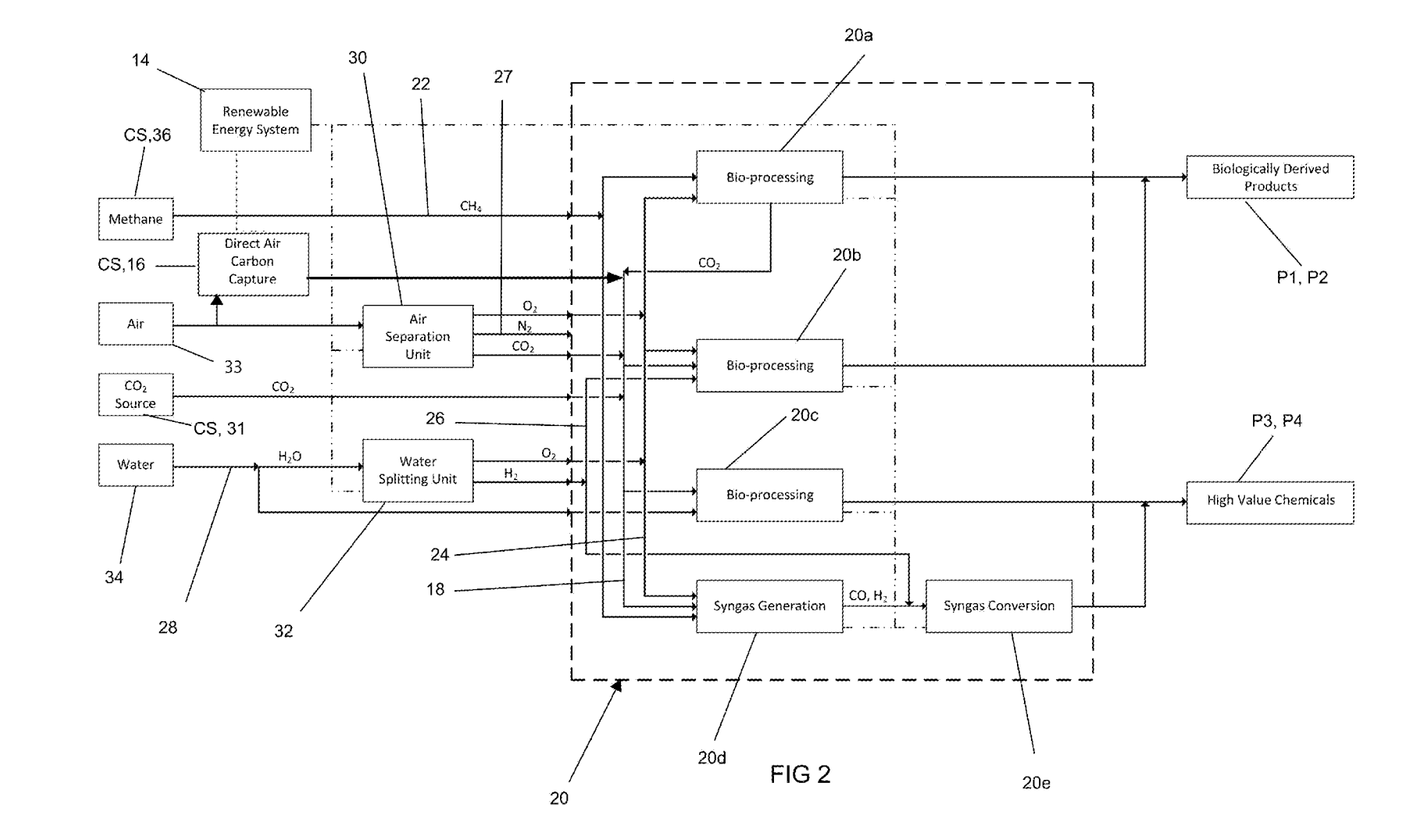
FIG. 2 is a more detailed flow diagram of the method and system shown in FIG. 1.

FIG. 2 depicts the overall system 10 in greater detail. In describing the system 10 the same reference numerals as used to denote the same features as in FIG. 1.

The renewable energy system 14 is able to provide energy to all plant and equipment of the system 10. Moreover, the energy system 14 can be arranged to provide different forms of energy to different plant and equipment in the system 10. For example, in one embodiment the energy system 14 may comprise a concentrated solar thermal (CST) plant heating a flowable heat transfer and storage medium such as molten salt and running for example at a temperature range of between 500° C. and 700° C. Alternately, or additionally, the renewable energy system 14 may comprises one, or a combination of one or more, of an array of photovoltaic cells; a wind turbine; and, a geothermal source.

The carbon source CS of FIG. 1 is shown in FIG. 2 as three different gaseous carbon compound sources. These are:
  direct air carbon capture system (DAC) 16 which is driven by the renewable energy system 14;
  a carbon dioxide source 31 which may for example include a supply of carbon dioxide as a by-product or waste product of an industrial process such as cement manufacture or an ammonium plant, or the combustion of a hydrocarbon; and
  a methane source 36 which may include methane: produced by processing of a hydrocarbon; or, as a biogas generated by the decomposition of organic waste. When the methane source is a biogas source then in addition to methane the source 36 will also provide gaseous carbon dioxide which may be processed by the processing plant 20.

The direct air carbon capture system 16 may use a carbon absorption material such as zeolite. The zeolite can be arranged in different banks which are heated and cooled at different times. At relatively low temperatures the carbon absorption material captures carbon dioxide from the air. On heating the captured carbon dioxide is released from the carbon absorption material in a substantially greater concentration than in the air. By appropriate control of the heating and cooling cycle of the different banks of zeolite or other carbon absorption material, a relatively constant carbon dioxide feed stream 18 can be produced.

Heated molten salt from the energy system 14 may be cycled through the direct air carbon capture system 16 to heat the zeolite and release the carbon dioxide. When the energy system 14 includes a CST plant, the system 10 may also include storage tanks (not shown) for the heated molten salt to enable a continuous circulation during a diurnal cycle. Alternately an electric heater powered by electricity from photovoltaic cells, and/or a wind turbine, and/or a geothermal source may be used to heat the zeolite.

The renewable energy system 14 may also provide electrical energy to the carbon processing plant 20 and other equipment of the system 10. This can be achieved in many different ways. For example, the heat transfer medium can be used to heat water to produce steam which in turn drives a turbine connected to a generator for producing electrical energy which is stored in onsite batteries. Alternately or additionally the renewable energy system 14 may also include a photovoltaic array for charging batteries. Electric current from the batteries can be used to power, on a 24/7 basis, other sections of the plant and equipment items of the system 10 including the carbon processing plant 20.

The system 10 includes an air separation unit (ASU) 30 which receives air from an air collection system 33, and a water splitting unit (WSU) 32, which may for example be in the form of an electrolyser. Both the ASU 30 and WSU 32 can be powered by electricity from the renewable energy system 14. The ASU 30 separates atmospheric air into its primary components which are mainly oxygen and nitrogen. The ASU 30 can be based on any known technology such as cryogenic air separation, membrane separation and pressure swing absorption. The oxygen from the ASU 30 constitutes or is added to the oxygen feed stream 24 for the carbon processing plant 20. Nitrogen and other gases produced by the ASU 30 can be purged to the atmosphere. Alternately if desired the nitrogen can be handled and/or used in numerous different ways including: captured and optionally liquefied as a further saleable product; or, delivered to and utilised within sections of the system 10 or plant 20 as feed stream 27.

The WSU 32 can be powered by electricity from the renewable energy system 14 to produce gaseous hydrogen and oxygen. The oxygen produced by the WSU 32 is added to the oxygen feed stream 24. The hydrogen produced by the WSU 32 is supplied as the hydrogen feed stream 26 to the carbon processing plant 20.

A water source 34 provides water to form the water feed stream 28. The feed stream 28 provides water to both the WSU 32 and the carbon processing plant 20.

Methane for the methane feed stream 22 is provided by a methane source 36. The methane source 36 may hold or supply methane from one or more of: a hydrocarbon reservoir, coal seam gas, or biogas for example from municipal or other organic waste. When the methane source 36 is a biogas source which produces both methane and carbon dioxide, then, as explained in greater detail in a later embodiment, the carbon dioxide can: be added to other CO2 feed streams; or by itself form the CO2 feed stream for the processing plant 20.

In this embodiment the carbon processing plant 20 includes five distinct carbon processing units 20a, 20b, 20c, 20d, and 20e. In any specific embodiment of the system 10, the carbon processing plant may include different combinations of the units 20a, 20b, 20c, 20d and 20e. This is dependent on the sources CS provided or available and the desired products. By way of non-limiting example, the carbon processing plant 20 in a particular embodiment may comprise: (a) units 20a and 20b; (b) units 20a and 20c; (c) units 20a, 20b and 20c, (d) units 20a, 20d and 20e; (e) units 20d and 20e; or all of 20a, 20b, 20c, 20d, and 20e.

The carbon processing unit 20a is a bioprocess that utilises methanotrophic bacteria to oxidise methane. Oxygen is also supplied to the unit 20a to facilitate the oxidation of the methane. An example of a biologically derived product, P1, of this bioprocess is a single cell protein which may be used as animal feed, such as but not limited to, pig or fish feed. A by-product of the reaction is carbon dioxide. This carbon dioxide is added to the carbon dioxide feed stream 18 for use in other areas of the carbon processing plant, such as, but not limited to, the processing unit 20b. This provides an integration aspect to the system 10 and method 12 as gaseous carbon by-products from one process is consumed in another to convert gaseous carbon by-product to carbon neutral/negative products.

The carbon processing unit 20b is a bioprocess utilising hydrogenotrophic bacteria which consumes carbon dioxide in the presence of hydrogen, oxygen and water to produce a second different biologically derived product P2 in the form of a single cell protein which may be used as animal feed, including pig feed and fish feed.

The carbon processing unit 20c is a bioprocess which yields photosynthetic cyanobacteria from light, carbon dioxide and water. High-value products, P3, can be extracted from the cyanobacteria in a controlled environment. Examples of high-value products include pharmaceuticals (e.g., anti-cancer drugs), nutraceuticals (e.g., health supplements), food additives, and animal feed in the form of single cell protein.

The carbon processing units 20d and 20e are used in combination to produce products P4 being high-value chemicals such as ethanol and isopropanol.

The carbon processing unit 20d is a syngas generation unit. This unit transforms carbon dioxide and methane provided by feed streams 18 and 22 respectively, optionally in the presence of oxygen to produce a synthesis gas (syngas), which is a mixture of hydrogen, carbon and its oxides, water and residual methane. The unit 20d may be a reforming reactor using heat produced from energy from the energy conversion system 14. A downstream syngas conversion unit 20e, transforms the synthesis gas into high-value chemicals P4. In one example the unit 20e may be a bioreactor in which the syngas is fermented resulting in the production of high-value chemicals such as ethanol and isopropanol. Alternately the unit 20e may conduct a thermochemical process such as a Fischer-Tropsch like process, to produce hydrocarbons. Additional hydrogen from the hydrogen feed, steam 26, can be provided to the unit 20e and used to adjust the ratio of hydrogen to carbon monoxide in the feed steam from unit 20d.

It should be noted here that some of the products or by-products of the some of the carbon processing units 20a-20e are used by other ones of the carbon processing units. For example, carbon monoxide and hydrogen produced by the unit 20d is fed as an input to the unit 20e. The carbon dioxide produced by the unit 20a can be combined with the carbon dioxide from direct air capture system 16 to feed to the carbon processing unit 20b, 20c and 20d.

The system 10 and method 12 include a control system having various sensors, gas detectors, flow controllers and valves for controlling the flow rate, volume and pressure of the carbon dioxide, methane, oxygen, hydrogen and water feed streams 18, 22, 24, 26 and 28 respectively to ensure the optimal stoichiometric and/or mass balancing of the feed streams to each of the carbon processing units 20a-20e in the carbon processing plant 20. The control system is also arranged to monitor and control the renewable energy system 14 for the production and storage of energy and delivery of energy to various plants, systems and equipment of the system 10.

Figure 3:
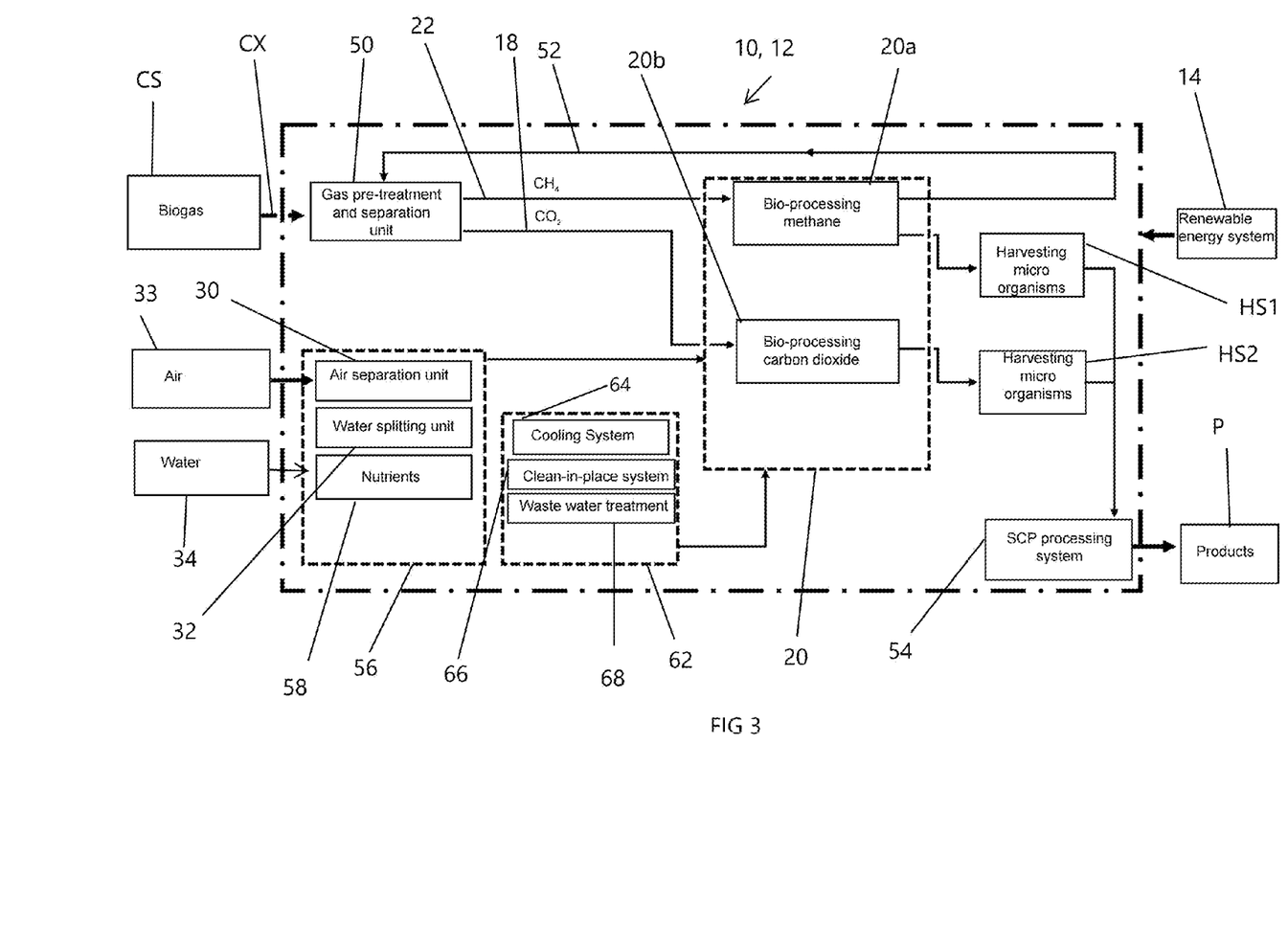
FIG. 3 is a flow diagram of a second embodiment of the disclosed system and method which may be designated as an integrated system and method for converting gaseous carbon compounds to carbon neutral or negative products where the gaseous carbon compounds comprise a mixture of methane and carbon dioxide emanating from a single source.
Figure 4:
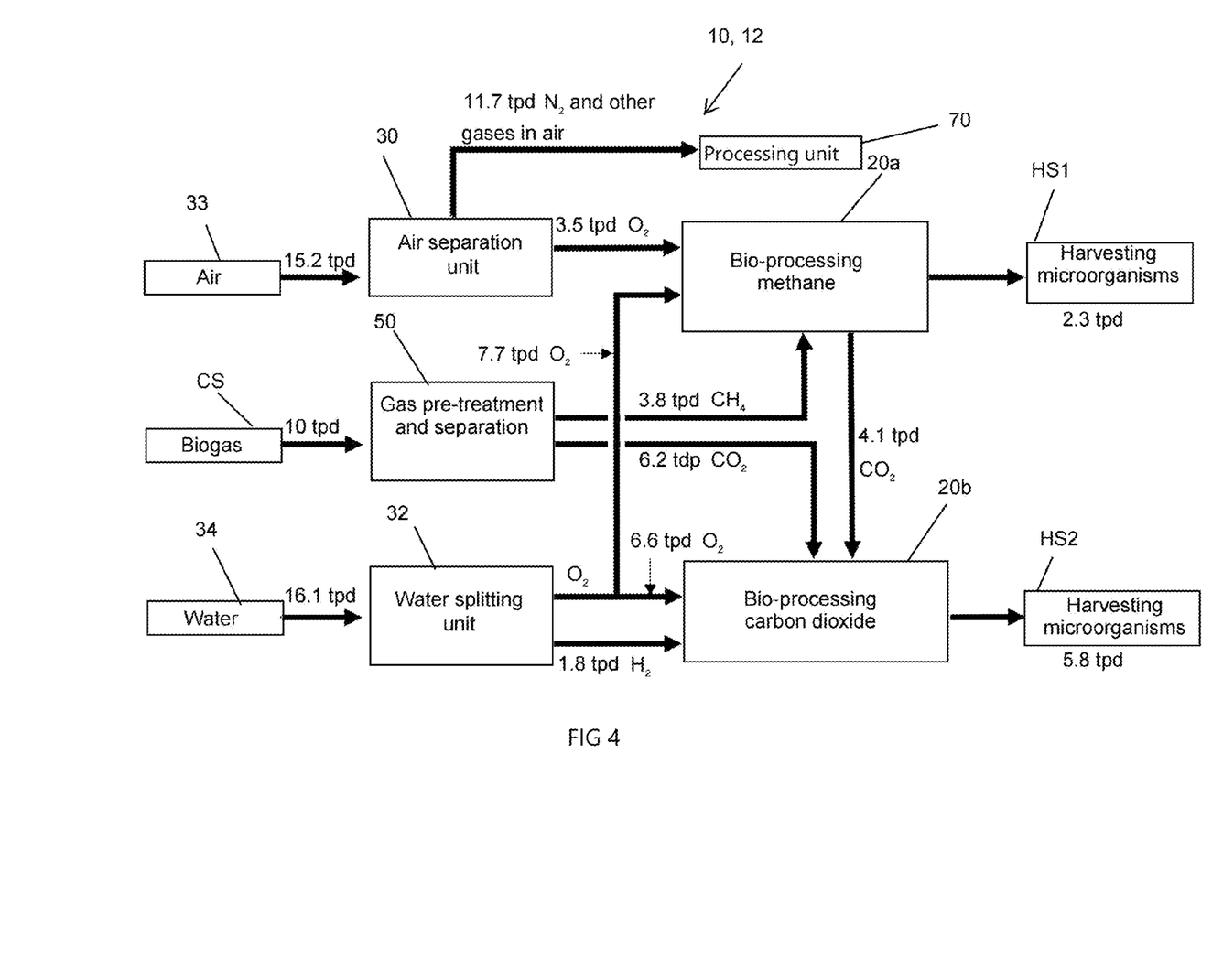
FIG. 4 is a mass flow diagram for the embodiment shown in FIG. 3.

FIGS. 3 and 4 are illustrative of an integrated biological carbon processing system 10 and method 12 for converting gaseous carbon compounds to carbon neutral or negative products. In describing this embodiment, the same reference numbers will be used to designate the same systems or processes used in describing the first embodiment shown in FIGS. 1 and 2. A renewable energy system 14 provides power for the system 10 and method 12 in the same manner as described in relation to the first embodiment.

In this embodiment there is a single mixed gaseous carbon source CS. The source may take the form of a biogas source. The source CS produces a gaseous feed stream CX as a mixture of gaseous carbon compounds, in particular methane and carbon dioxide. The feed stream CX may also include other gases such as nitrogen, hydrogen sulphide and ammonia. The feed stream CX is fed to a gas pre-treatment and separation unit 50. The unit 50 removes the non-carbon gases in the feed stream and separates the mixed gaseous carbon compounds into a high-purity methane feed stream 22 and carbon dioxide feed stream 18.

In this embodiment all processing of the gaseous carbon compounds is performed biologically in an integrated biological processing plant 20. The processing plant 20 comprises a biological methane processing/conversion system 20a and a biological carbon dioxide processing/conversion system 20b. The processing systems 20a, 20b use different microorganisms for processing their respective feed gases. The methane feed stream 22 is fed to the biological methane processing/conversion system 20a. The system 20a is in the form of a bioreactor having microorganisms that feed on methane, such as methanotrophs that metabolise methane as their source of carbon. Simultaneously the carbon dioxide feed stream 18 is fed to the biological carbon dioxide processing/conversion system 20b which consumes carbon dioxide. One example of this is a bioreactor containing hydrogenotrophic bacteria.

Non-consumed methane from, and carbon dioxide produced by, the process/system 20a are recycled back though conduit 52 to the gas pre-treatment and separation unit 50. In this way, the carbon dioxide produced by process 20a as a by-product is used as feed input to the process 20b.

The system 10 includes first and second harvesting systems HS1 and HS2 and a single cell protein (SCP) processing system 54 which together form a microorganism harvesting and processing system. The microorganisms grown in the processes 20a are harvested by the first harvesting system HS1 as a source of a first single cell protein. The microorganisms grown in the processes 20b are harvested by the second harvesting system HS2 as a source of a second product also in the form of single cell protein. The harvested single cell proteins are processed together in the single cell protein (SCP) processing system 54. This may include settling the proteins in a settling tank to achieve a paste like consistency, and a rotating drum for collecting the paste. The single cell protein (SCP) processing system 54 also includes a common dryer for drying the paste. The drying is conducted while the paste is on the drum. The paste may be dried to a desired moisture content, for example 6%-8% then converted into a single cell protein powder which forms the final end product P of the system 10, method 12.

The biological processes 20a and 20b may be aided or otherwise promoted by the addition of feedstocks via feedstock systems 56 which include, but not limited to, hydrogen, oxygen, water, ammonia, and nutrients. The feedstock systems 56 include an air separation unit 30 which produces gaseous oxygen, a water splitting system 32 which produces gaseous hydrogen and gaseous oxygen, and a nutrient system 58. An air collection system 33 supplies air to the air separation system 30. A water supply 34 (which can for example be a mains supply) supplies water to the water splitting system 32. The nutrient system 58 may supply macronutrients and/or micronutrients. The micronutrients may include but are not limited to cobalt, manganese, iron, zinc, chlorine, boron and vitamins. The macronutrients may include but are not limited to phosphorus, potassium, and nitrogen. Each of the systems within the feedstock system 56 are powered by the renewable energy system 14.

Auxiliary systems 62 are provided to assist in maintaining the operation of the integrated biological processing plant 20. The auxiliary systems 62 may include a cooling system 64, a clean-in-place system 66 and a waste water treatment system 68. The cooling system 64 operates to remove heat generated by the metabolic processes 20a, 20b. The cooling system 64 maintains the temperature within the reactors used in the processes 20a, 20b within the optimum activation range of the respective mesophilic bacterium. In one example the cooling system may be in the form of water jackets surrounding the respective reactors. The cooling system may provide different operating temperatures to the respective reactors for the processes 20a and 20b. Temperature control can be provided by electrically controlled temperature regulating devices powered by the renewable energy system 14.

The clean-in-place system 66 is used to periodically, or on demand, clean the reactors used to conduct the processes 20a, 20b. This may for example deliver water and/or steam and/or various chemicals to clean and sanitise the bioreactor including removing biofilm or other residue. The wastewater treatment system may treat water from one or more of the: clean-in-place system 66; SCP processing system 54; and the plant 20.

The size of bioreactors used in processes 20a, 20b is determined based on the gas supply and the amount of carbon dioxide that is recycled from process 20a to the unit 50 via conduit 52.

FIG. 4 which is provided for illustrative purposes only, is a mass flow diagram for the system 10, method 12 for a single mixed biogas source CS which produces 10 tonnes per day (tpd) mixed methane and carbon dioxide in a ratio of about 38:62 by weight. 3.8 tpd of methane and 6.2 tpd of carbon dioxide are fed from the gas pre-treatment and separation unit to the reactors performing the process 20a and 20b respectively. In addition, the process 20a produces about 4.1 tpd of CO2 as a by-product which is provided as addition feedstock to the process 20b.

Air and water are supplied at about 15.2 tpd and 16.1 tpd respectively to produce the required mass flow of oxygen and hydrogen to support the processing of the methane and carbon dioxide. The methane processing/conversion system 20a receives 3.5 tpd of oxygen from the air separation unit 30, and 7.7 tpd of oxygen from the water splitting unit 32. The water splitting unit 32 also supplies 6.6 tpd of oxygen and 1.8 tpd of hydrogen to the carbon dioxide processing/conversion system 20b. With these mass flows, about 2.3 tpd of single cell protein is produced by the system 20a, and about 5.8 tpd of single cell protein is produced by the system 20b. Nitrogen and other gases produced by the air separation unit are discharged at a rate of about 11.7 tpd and processed by a processing unit 70. This may include for example capturing the nitrogen as a gas or liquifying the nitrogen which may then be sold to a third party.

All of the methanotrophic, cyanobacteria, and hydrogenotrophic bacteria may be mesophilic bacterium, optimally operating in temperature range of about 15°-45° C. The processes and material flows in embodiments of the system 10 and method 12 may be conducted at atmospheric pressure. The doubling growth rate of bacterium under these conditions may vary between 2-8 hours.

The system and method describe with reference to FIGS. 3 and 4 is well suited for animal husbandry, for example in a piggery, as a closed loop biogas processing system capable of producing animal feed material, i.e., single cell protein, derived from the animal waste products. This is a carbon negative process as it consumes the greenhouse gases methane and carbon dioxide that would otherwise be emitted by the decomposition of the waste products, and uses renewable energy as its source of power.

As should be evident from the above description the embodiment shown in FIGS. 3 and 4 is in substance a subset of the system shown in FIGS. 1 and 2 using the bioprocesses 20a, and 20b and/or 20c, a renewable energy system 14, and inputs of air and water to feed an air separation unit 30 and water splitting unit 32 respectively, and producing single cell protein. The system 10 of FIGS. 3 and 4 can be augmented or modified by addition of the carbon processing units 20d and 20e, and/or additional gaseous carbon compound sources.

While an exemplary embodiment has been presented in the foregoing detailed description, it should be appreciated that a vast number of variations exist. For example, in the system 10 shown and described in relation to FIGS. 3 and 4, the bioprocess used to consume the carbon dioxide is performed by hydrogenotrophic bacteria. However, as an alternative, or indeed in addition, the bioprocess may comprise the previously described process 20c, utilising photosynthetic cyanobacteria to consume gaseous carbon dioxide in the presence of water to produce high-value products, such as pharmaceuticals (e.g. anti-cancer drugs), nutraceuticals (e.g. health supplements) and food additives. In another variation, in addition to, or as an alternative for the WSU 32, the system 10 may include a methane pyrolysis unit for the purpose of producing hydrogen gas. Similarly, the gaseous carbon dioxide feed stream 18 can utilise or otherwise be fed with gaseous carbon compounds from one or more of multiple sources, including but not limited to: the DAC 16; an acid gas removal unit of a liquid natural gas processing plant; the production, processing or combustion of a fossil fuel; the by-product or waste product of industrial plants such as, but not limited to, cement manufacture plants and, ammonia production plants. Moreover, embodiments of the system 10 and method 12 may be provided as facilities added to existing any industrial production plants that produces gaseous carbon compounds as a by-product or waste product to produce additional valuable products. When used in this way the capacity of renewable energy system may be expanded to also power the industrial production plant and thus further assist in reducing the carbon footprint of the plant. In another variation to the system described with reference to FIGS. 3 and 4, the microorganism harvesting and processing system may comprise a separate processing system 54 for each of the harvesting systems HS1 and HS2, rather than a common processing system 54. It should also be appreciated that the exemplary embodiments of the system and method are only examples, and are not intended to limit the scope, applicability, or configuration of the present disclosure in any way. Rather, the foregoing detailed description will provide those skilled in the art with a convenient road map for implementing an exemplary embodiment of the disclosed system and method.

In the claims which follow, and in the preceding description, except where the context requires otherwise due to express language or necessary implication, the word "comprise" and variations such as "comprises" or "comprising"

are used in an inclusive sense, i.e. to specify the presence of the stated features but not to preclude the presence or addition of further features in various embodiments of the system and method as disclosed herein.

What is claimed:

1. An integrated system for converting gaseous carbon compounds to carbon neutral or negative products, the system comprising:
one or more units that produce respective reactants;
one or more sources of carbon dioxide and methane;
a biological methane processing system containing methane metabolising microorganisms and fed with methane from the one or more sources, and one or more of the reactants, wherein the biological methane processing system:
propagates methane metabolising microorganisms; and
produces carbon dioxide as a by-product;
a biological carbon dioxide processing system containing carbon dioxide metabolising microorganisms and fed with carbon dioxide from the one or more sources, the carbon dioxide by-product, and one or more of the reactants, wherein the biological carbon dioxide processing system propagates carbon dioxide metabolising microorganisms;
a microorganism harvesting and processing system that:
harvests the methane metabolising microorganisms propagated by the biological methane processing system;
harvests the carbon dioxide metabolising microorganisms propagated by the biological carbon dioxide processing system; and
produces a single cell protein; and
a control system that controls flow of the carbon dioxide, methane and the reactants to the biological methane processing system and the biological carbon dioxide processing system to provide mass balanced quantities of the carbon dioxide and methane and reactants for processes performed in each of the biological methane processing system and the biological carbon dioxide processing system.

2. The integrated system of claim 1, further comprising:
a renewable energy system that converts energy from one or more renewable energy sources into one or more forms of controlled energy;
wherein the biological methane processing system, the biological carbon dioxide processing system and the one or more units for producing respective reactants are powered by the controlled energy.

3. The integrated system of claim 2, wherein the control system is further arranged to monitor and control the renewable energy system for the production and storage of energy and delivery of energy to the biological methane processing system and the biological carbon dioxide processing system and the one or more units for producing respective reactants.

4. The integrated system of claim 2, further comprising a cooling system that cools one or both of the biological methane processing system and the biological carbon dioxide processing system to operate within a predetermined temperature range, wherein the cooling system and the microorganism harvesting and processing system are powered by the controlled energy.

5. The integrated system of claim 1, wherein one of the units for producing respective reactants is an air separation unit that produces a gaseous oxygen, and the integrated system is arranged to feed the gaseous oxygen to one or both of the biological methane processing system and the biological carbon dioxide processing system.

6. The integrated system of claim 1, wherein one of the units for producing respective reactants is a water separation unit that produces further gaseous oxygen, and the integrated system is arranged to feed the further gaseous oxygen to one or both of the biological methane processing system and the biological carbon dioxide processing system.

7. The integrated system of claim 6, wherein the water separation unit produces gaseous hydrogen, and the integrated system is arranged to feed the gaseous hydrogen to the biological carbon dioxide processing system.

8. The integrated system of claim 1, further comprising a cooling system that cools one or both of the biological methane processing system and the biological carbon dioxide processing system to operate within a predetermined temperature range.

9. The integrated system of claim 1, wherein the microorganism harvesting and processing system includes:
a common dryer that dries products produced by the biological methane processing system and the biological carbon dioxide processing system, the products comprising the single cell protein.

10. The integrated system of claim 1, wherein the one or more sources of carbon dioxide and methane comprises:
(a) respective separate sources of carbon dioxide and methane; or
(b) a source that produces a mixture of carbon dioxide and methane.

11. The integrated system of claim 1, wherein the methane metabolising microorganisms comprise mesophilic methanotrophic bacterium.

12. The integrated system of claim 1, wherein the carbon dioxide metabolising microorganisms comprise mesophilic bacterium.

13. The integrated system of claim 12, wherein the carbon dioxide metabolising microorganisms comprise cyanobacteria.

14. The integrated system of claim 13, wherein the carbon dioxide metabolising microorganisms comprise hydrogenotrophic bacteria.

15. The integrated system of claim 1, further comprising at least a first carbon processing system wherein the carbon dioxide by-product is fed to the first carbon processing system and the first carbon processing system produces a syngas.

16. The integrated system of claim 15, further comprising a second carbon processing system downstream of the first carbon processing system, wherein the second carbon processing system transforms the syngas into a high value chemical.

17. The integrated system of claim 16, wherein the second carbon processing system comprises a bioreactor arranged to ferment the syngas to form the high value chemical.

18. The integrated system of claim 16, wherein the second carbon processing system is arranged to conduct a thermochemical process.

19. The integrated system of claim 1, wherein the one or more sources of carbon dioxide and methane comprise one or more sources of mixed carbon dioxide and methane gas.

* * * * *